United States Patent [19]

Schwartz et al.

[11] 4,034,035

[45] July 5, 1977

[54] METHOD OF PREPARING MULTI-TONED TABLETS

[75] Inventors: Joseph B. Schwartz, Hatfield; Frederick A. Restaino, Hatboro, both of Pa.

[73] Assignee: Merck & Co., Inc., Rahway, N.J.

[22] Filed: July 14, 1975

[21] Appl. No.: 595,645

[52] U.S. Cl. ............................................ 264/77
[51] Int. Cl.² .......................................... B29C 9/00
[58] Field of Search ............... 264/115, 122, 77, 78

[56] References Cited

UNITED STATES PATENTS 3,436,453  4/1969  Vincent, Jr. et al. ............... 264/78
3,655,852  4/1972  Koff et al. ........................ 264/115

*Primary Examiner*—Robert F. White
*Assistant Examiner*—James R. Hall
*Attorney, Agent, or Firm*—Frank M. Mahon; Harry E. Westlake; Rudy J. Anderson

[57] ABSTRACT

Multitoned compressed tablet forms of pleasing and distinctive appearance are obtained in a single granulation and coloring step by treating an excipient mixture of microcrystalline cellulose and modified corn starch containing a therapeutically effective quantity of an active drug or drugs with a granulating solution containing a water soluble dye suitable for pharmaceutical application. Work-up of the wetted granulation by usual wet granulation techniques followed by compression of the finished granules results in a distinctive multitoned tablet form.

3 Claims, No Drawings

METHOD OF PREPARING MULTI-TONED TABLETS

This invention relates to new and useful orally administratable tablets having a distinctive appearance. More particularly, the instant invention relates to novel multitoned, non-coated, non-enteric compressed tablets suitable for oral administration in pharmaceutical and other applications requiring oral administration and to the process for preparing such tablets.

It is well recognized in the pharmaceutical arts that there is an authentic, and, indeed, sometimes an urgent, need for an effective means of identification for drug products. Such means of identification for drug products is important not only as an identification of the source of the drug product (identification of the manufacturer), but in preventing errors in the manufacturing and packaging of drug products; in the dispensing of drug products; and in the identification and control of poisons. Further, distinctive identification of drug products plays a significant role in the prescribing of drug products.

As pointed out in an editorial appearing in Clinical Pharmacology and Therapeutics, Vol. 13, No. 2, 157-158 (March-April 1972), by John Mazzullo, M.D., it is within the experience of all physicians having contact with outpatients to have their planned therapeutic regimen hopelessly confounded by a patient's confusion due to the similar size, shape or color of the tablets prescribed. Concluding that the more distinctive the pill is, the easier and safer it is to use, the author points out that, because of the likelihood of pharmaceutical drug-drug interactions, each manufacturer should strive to develop distinctive tablet forms for its products.

In attempting to combat the problem of confusion and to establish distinctive tablet forms for their products, pharmaceutical manufacturers have employed, and are employing, a variety of tablet shapes, sizes and colors. Handicaped, however, by practical limitations as to useful tablet shape and size and by severe and increasing limitations as to pharmaceutically acceptable tablet colorant materials, confusion in tablet shape size and color persists. The imprinting of coded symbols on tablet dosage forms, although capable of positively identifying both the manufacturer and the drug product contained in the tablet, is not wholly effective as a means whereby the patient can identify, and distinguish between drug products, partly because of the patient's unfamiliarily with the symbols employed and partly because many patients, particularly the elderly and those suffering from impared vision, cannot make out the identifying inscription.

Other attempts to achieve distinctive tablet appearance have involved the preparation of tablets which may be characterized as multicolored. Such tablets have been, and are being, actively employed in the pharmaceutical industry as a means of obtaining distinctive tablet dosage forms (see, for example, the tablets described in U.S. Pat. No. 2,996,431, Aug. 15, 1961 and U.S. Pat. No. 3,044,938, July 17, 1962). Tablets of this type are characterized by having a multicolored, speckled (variegated) appearance. By employing varying combinations of colorants, tablets have been produced by the techniques of the cited patents which not only are pleasing to the eye, but which are distinctive in appearance and capable of establishing positive product identification. Although possessing desirable characteristics, these multicolored, speckled tablets of the prior art are obtainable only by manufacturing techniques which involve the preparation, for each colorant variation desired, of separately dyed granulations or particles and the blending of such separately dyed granulations or particles in order to achieve the desired speckled effect. Thus, the variegated color effect of the prior art tablets is achieved only at the expense of a plurality of time consuming and costly processing steps. The techniques of the instant invention, in contrast, make possible the preparation of multitoned, speckled tablets of pleasing and distinctive appearance in a single granulation and coloring step.

It is the object of the instant invention, therefore to prepare a multitoned compressed tablet dosage form having a distinctive speckled (variegated) color by a controlled and easily reproducible process which involves only a single granulating and coloring step and which may be carried out with conventional tableting apparatus. The term, "multitoned", as used herein to describe the tablets prepared by the techniques of the instant invention means that the speckled (variegated) color imparted to the tablets is achieved by gradations of a single basic color. The tablets so produced, therefore, are a multitoned rather than multicolored in the usual sense.

The instant invention is based upon applicants' discovery that when a water soluble dye is incorporated into a conventional granulating solution and this solution is then applied to an excipient mixture of microcrystalline cellulose and a modified corn starch (as hereinafter defined) into which has been blended a therapeutically effective quantity of the desired active drug or drugs, the dye solution is preferentially attracted to the starch component as opposed to the cellulose. After work-up of the wetted granulation mixture in the conventional manner and the usual drying, milling, sizing steps, compression of the finished granules to any desired shape and size, usually in the presence of a suitable lubricant, results in a multicolored tablet of pleasing and distinctive appearance where the speckled (variegated) color effect is achieved through various gradations of the single basic color.

The excipient mixture employed in forming the granulation is a critical aspect of the instant invention essential to achieving the multitoned effect in the finished compressed tablet. The microcrystalline cellulose employed in the excipient mixture is a standard article of commerce well-known to those skilled in the art. A suitable material for example, is available as AVICEL from Food Machinery Corporation, Avicel Division, Marcus Hook, Pa. The modified corn starches suitable as excipient materials according to the instant invention are those modified corn starches characterized by having a cold water solubles content in excess of 10% by weight. Suitable commercially available modified corn starches of this type include, for example STA RX 1500, E. M. Stanley Co., Decatur, Ill., ALMIDON ESPECIAL, Productos De Maiz S.A. (Corn Products Co.), Mexico, LAMALIN ED 200, Laxmi Starch Co., Ltd., Bombay, India, NATIONAL STARCH 78-1713, National Starch & Chemical Corporation, New York, New York. No additional excipient is required in order to form granules suitable for compression and the microcrystalline cellulose and modified corn starch may be employed as obtained commercially without further modification.

The microcrystalline cellulose and the modified corn starch may be mixed in varying proportions to obtain excipient mixtures suitable for granulation and subsequent compression. Satisfactory results usually are obtained when the weight ratio of microcrystalline cellulose to modified corn starch is about 1:3 to 3:1. Preferred granulation mixtures contain an equal (i.e. 1:1) mixture of the cellulose and starch. The color intensity obtained in the final tablet is primarily a function of the particle size of the granules subjected to granulation, larger granules giving rise to higher color intensity. Pleasing and distinctive multitoned appearance is usually achieved when the colored granules are milled to particle sizes between 325 to 30 mesh, U.S. Standard Sieve (e.g. 95% passing the 30 mesh sieve). The dried and sized granules then are blended with about 0.1 to about 5% by weight of a conventional tableting lubricant, such as, for example, calcium or magnesium stearate, and compressed in standard tableting machines to any desired shape and size.

The coloring materials employed for pharmaceutical applications preferably are certified water soluble food colors. Any water soluble non-toxic and pharmaceutically approved coloring material, however, may be employed. Typical certified water soluble dyes which may be employed will include, for example, F.D.&C. Red No. 2, F.D.&C. Red No. 40, F.D.&C. Blue No 1, F.D.&C. Blue No. 2, F.D.&C. Yellow No. 5, F.D.&C. Yellow No. 6, F.D.&C. Green No. 3, F.D.&C. Orange No. 4, and mixtures of these. The selected dye usually from about 0.5 to 2.0 parts by weight, is dissolved in a conventional granulating solution (typical is an aqueous alcohol solution wherein the ratio of alcohol to water ranges from about 1:3 to 1:1) and the colored granulating solution is then employed to wet the dry granulation mixture in the usual manner.

The instant invention is applicable to a wide variety of pharmaceutical actives. Indeed, practically all types of tabletable medicaments, both water soluble and water insoluble, may be employed. Typical of useful medicinal agents include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform agents such as chlorisondamine and the like, tranquilizers and muscle relaxants such as fluphenazine; chlorpromazine, triflupromazine, mephenesin, meprobamate and the like, antihistamines such as diphenhydramine, dimenhydrinate, tripelennamine, perphenozine, chlorprophenozine, chlorprophenpyridamine and the like, hypotensive agents such as rauwolfia, reserpine and the like, carioactive agents such as benzyldrofluanthiazide, slumethiazide, chlorothiazide, aminotrate and the like, steroids such as testosterone, fludrocortisone, triamcinolone, cortisone prednisolone and the like, antibacterial agents, e.g., sulfonamides such as sulfadiazine, sulfamerazine, sulfisoxazole and the like, antimalarials such as chloroquine and the like, antibiotics such as tetracyclines, nystatin, streptomycin, penicillin, grisofulvin and the like, sedatives such as chloral hydrate, phenobarbitol and other barbiturates, gluthethimide, antitubercular agents such as isoniazid and the like, analgesics such as asprin, meperidine and the like, insulin polypeptides, vatimines and enzymes, blood products and the like. The selected medicinal agent, or mixture of medicinal agents, is blended with the excipient microcrystalline cellulose/modified corn starch mixture prior to wetting with the granulating solution. The actives may be employed in concentration up to about 30% by weight of the finished tablet. Usually, however, the actives will constitute from about 1 to about 5% by weight of the finished tablet.

As will be evident from the foregoing, the tablets of this invention are prepared by conventional wet-granulation techniques employing the specific excipient mixture disclosed and described herein and making use of standard tablet manufacturing equipment. The wet-granulation process generally involves the steps of weighing, blending, granulating, drying, milling, lubrication and compression. Thus, multitoned tablets typical of the instant invention may be prepared by (1) blending to a uniform admixture equal parts of microcrystalline cellulose and modified corn starch as described above; (2) adding sufficient active medicinal to the blended excipient to give the desired active concentration in the finished tablet and blending the active and excipient to uniform admixture; (3) dissolving the selected water soluble dye (about 1 part by weight) in an aqueous alcohol (1:1 alcohol to water) granulating solution; (4) adding the colored granulating solution to the dry granulation blend with continuous mixing until the mass has achieved the proper consistency for granulation; (5) drying the granulation mass (conveniently in an oven at about 40° to about 50° C. overnight); (6) milling the dry granulation mass to the desired particle size; (7) lubricating the milled and sized granules with a conventional tabletting lubricant; and (8) compressing the lubricated granules to any desired shape and size. The tablets so produced will display the desired distinctive and pleasing multitoned appearance heretofore described.

As pointed out above, the instant invention provides a means for achieving multitoned tablet forms of distinctive and pleasing appearance by a simple, reproducible and economic process involving only a single granulation and coloring step: the multiple coloring and granulating steps characteristic of the prior art multicolored tablets being eliminated. The technique of the instant invention thus increases the number of different and distinctive appearing tablet forms available to the pharmaceutical manufacturer from the limited number of coloring materials suitable for pharmaceutical applications.

Although the instant invention has been described in the foregoing specification primarily in terms of its pharmaceutical application, it will be obvious to anyone skilled in the art that the instant invention can be applied readily to the preparation of tablets intended for nonpharmaceutical applications. Typical of such obvious nonpharmaceutical applications would be, for example, the preparation of toxic oral dosage forms intended for pesticidal applications. Applicants consider all such obvious modifications and applications to be the full equivalent of the invention described herein and to fall within the scope of the instant invention.

The subject matter which applicants regard as their invention is particularly pointed out and distinctly claimed as follows:

1. A process for preparing multi-toned compressed tablet dosage form which comprises:
   a. blending to a uniform admixture a therapuetically effective quantity of an orally administerable medicament together with an excipient mixture of microcrystalline cellulose and modified corn starch having a cold water soluble content in excess of 10 percent to form a dry mass for granulation;

b. adding to said dry mass with continual mixing a granulation solution having dissolved therein a water soluble pharmaceutically acceptable dye until the thus wetted mass has achieved the proper consistency suitable for granulation and wherein the dye has been more strongly attracted to the starch excipient than to the cellulose excipient;

c. drying the wetted mass;

d. milling the dried mass so produced to obtain granules having a particle size between about 30 to about 325 mesh;

e. compressing the dried granules so obtained to the desired tablet shape and size to form multi-toned compressed tablet dosage forms.

2. The process of claim 1 wherein the ratio of microcrystalline cellulose to midified corn starch in the excipient mixture is about 3:1 to 1:3 by weight.

3. The process of claim 2 wherein the ratio of microcrystalline cellulose to modified corn starch in the excipient mixture is about 1:1 by weight.

* * * * *